United States Patent [19]
Eckhaus

[11] Patent Number: 5,894,584
[45] Date of Patent: Apr. 13, 1999

[54] SYSTEM FOR WRITING DIGITIZED X-RAY IMAGES TO A COMPACT DISC

[75] Inventor: Neal Eckhaus, Rochester, N.Y.

[73] Assignee: Eastman Kodak Company, Rochester, N.Y.

[21] Appl. No.: 08/704,060

[22] Filed: Aug. 28, 1996

[51] Int. Cl.$^6$ .................................................. G06F 13/00
[52] U.S. Cl. ............................................. 395/821; 711/117
[58] Field of Search ................................ 395/821, 872, 395/855; 711/117

[56] References Cited

U.S. PATENT DOCUMENTS

| | | | |
|---|---|---|---|
| 5,276,840 | 1/1994 | Yu | 395/855 |
| 5,586,264 | 12/1996 | Belknap et al. | 395/200.08 |
| 5,652,614 | 7/1997 | Okabayashi | 395/200.49 |
| 5,715,424 | 2/1998 | Jesionowski et al. | 395/182.22 |

Primary Examiner—Ayaz R. Sheikh
Assistant Examiner—Xuong Chung-Trans
Attorney, Agent, or Firm—Peyton C. Watkins

[57] ABSTRACT

A system for writing data to a storage media comprises a data acquisition device for acquiring digitized data; a media writing device for inputting the digitized data to the storage media; and a computer comprising a first microprocessor for controlling operations of the computer; a first storage device for receiving and storing the digitized data from said data acquisition device; and a second storage device for receiving and storing the digitized data from the first storage device, and for transferring the digitized data to the writing device after the first storage device transfers the digitized data to the second storage device for substantially eliminating writing errors.

8 Claims, 2 Drawing Sheets

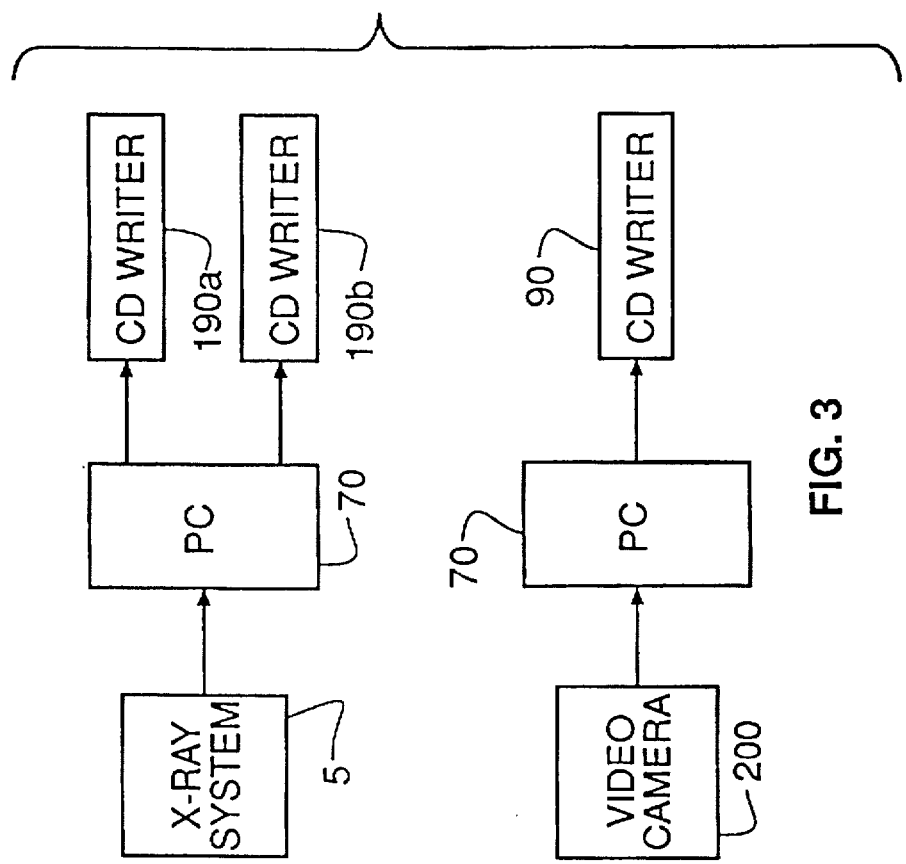
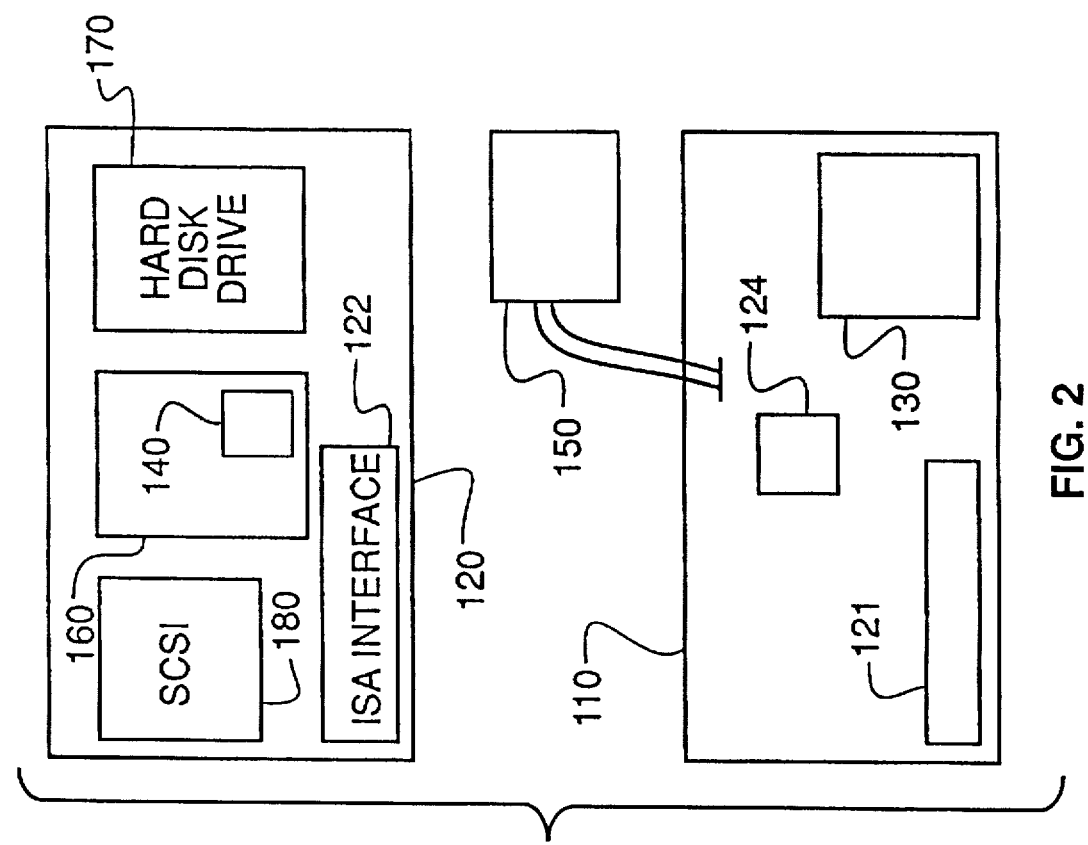

SYSTEM FOR WRITING DIGITIZED X-RAY IMAGES TO A COMPACT DISC

FIELD OF THE INVENTION

The invention relates generally to the field of writing digitized x-ray images to a compact disc and, more specifically, to writing the x-ray images by storing the images into a buffer dedicated to storage for substantially eliminating writing errors due to data interruptions to the compact disc.

BACKGROUND OF THE INVENTION

A digital x-ray image capture system typically includes a x-ray source that directs x-rays through a subject and onto an image capturing device for capturing an image of the subject in digitized form. The digitized data is sent over a fiber optic cable to a computer for permitting image processing on the digitized data and for, ultimately, storing the processed data on a memory storage device.

A compact disc writer then receives the processed data from the memory storage device and writes it to a compact disc which, in a single track format, writes the data sequentially and helically along the disk, as is well known in the art. Once writing is initiated, the compact disc writer requires the data be in a continuously and uninterrupted bit stream until completion of the writing process.

Although the presently known and utilized system is satisfactory, it is not without drawbacks. If additional images are sent to the computer while the computer is transferring data to the compact disc writer, the data transfer to the compact disc writer can be temporarily interrupted causing a writing error, generally referred to in the art as buffer underrun.

Consequently, a need exists for improvements in the construction and mode of operating the digital x-ray image capture system so as to overcome the above-described drawbacks.

SUMMARY OF THE INVENTION

The present invention is directed to overcoming one or more of the problems set forth above. Briefly summarized, according to one aspect of the present invention, the invention resides in a system for writing data to a storage media comprising (a) a data acquisition device for acquiring digitized data; (b) a media writing device for inputting the digitized data to the storage media; and (c) a computer comprising: (c1) a first microprocessor for controlling operations of said computer; (c2) a first storage device for receiving and storing the digitized data from said data acquisition device; and (c3) a second storage device for receiving and storing the digitized data from the first storage device, and for transferring the digitized data to said writing device after the first storage device transfers the digitized data to the second storage device for substantially eliminating writing errors.

It is an object of the present invention to provide a system for writing digitized x-ray images to a compact disc which substantially eliminates writing errors due to data interruptions to the compact disc.

It is an advantage of the present invention to provide a computer-insertable card for easily retrofitting existing computers.

It is a feature of the present invention to provide a storage device dedicated to receiving and storing the digitized images.

The above and other objects of the present invention will become more apparent when taken in conjunction with the following description and drawings wherein identical reference numerals have been used, where possible, to designate identical elements that are common to the figures.

BRIEF DESCRIPTION OF THE DRAWINGS

FIG. 2 is a schematic diagram of personal computer cards of the present invention; and FIG. 3 is an alternative embodiment of the present invention.

DETAILED DESCRIPTION OF THE INVENTION

Figure 1:
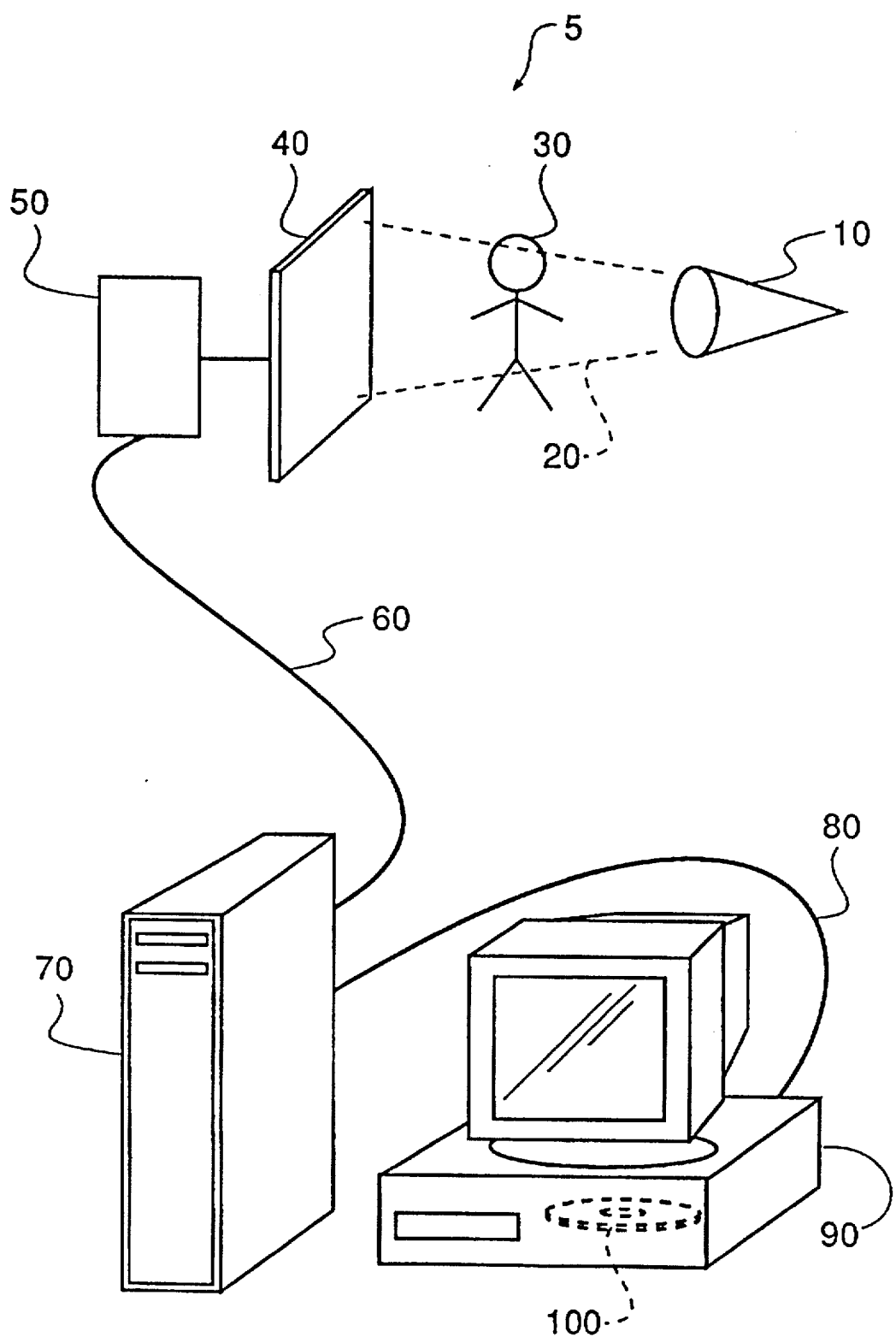
FIG. 1 is a perspective view of a system for capturing and permanently storing digitized x-ray images.

As used herein, a computer readable storage medium includes, for example, magnetic storage media such as a magnetic disk (such as a floppy disk) or magnetic tape; optical storage media such as optical disk, optical tape, or machine readable bar code; solid state electronic storage devices such as random access memory (ROM), or read only memory (RAM); or any other physical device or medium employed to store a computer program or computer data.

Referring to FIG. 1, there is illustrated a system 5 for storing images captured by a digitized x-ray system. The digitized x-ray system includes a x-ray source 10 which projects x-rays 20 onto and through the subject 30 and finally onto a sensor 40 for capturing a digital representation of the image on the sensor 40, as is well known in the art. The sensor 40 sends the digital representation to any suitable transmission device 50 where it is temporarily stored. If desired, the above-described, image capture procedure is then repeated until a suitable number of digital representations are stored; the preferred embodiment described herein illustrates the capturing of a plurality of images.

The user then manipulates the transmission device 50 for instructing it to send all of the digital representations over fiber optic cable 60 to a tower-based personal computer (PC) 70, which performs image processing on the digital representations by any wellknown image processing software stored on a computer readable storage medium (not shown in FIG. 1), as is well known in the art. After the image processing, the digital representations of the image are stored, as will be described in detail below.

The digital representations are then sent in a continuous and uninterrupted bit stream over a cable 80 to a compact disc writer 90, such as a "KODAK" 6X CD writer, where the data is written to a compact discread only memory (CD-ROM) 100. The CD-ROM 100 may then be removed for permitting the image to view on other visual display devices, as is well known in the art.

Referring to FIG. 2, there is illustrated a schematic diagram of a PC motherboard 110 which is mounted in the tower-based PC 70, and a PC card 120 which is placed in a slot 121 of the motherboard 110. Both the motherboard 110 and card 120 include an ISA interface 122 and 124 for permitting communication with each other and other components (not shown) of the PC 70. A first microprocessor 130 is included on the motherboard 110 which, in conjunction with a second microprocessor 140 on the card 120, controls and directs the operations of the computer.

After the image processing is complete, the first microprocessor 130 directs the image processing software to store the digital representations on a first computer readable storage medium 150, and then, after all the images are completely stored, sends a signal to the second microprocessor 140 that the images are stored on the first storage medium 150. It is instructive to note that, if additional images are sent to the tower-based PC 70 during storage of the data to the first storage medium 150, the first microprocessor 130 will be temporarily interrupted causing the bit stream of data into the first storage medium 150 to be discontinuous. However, writing errors do not occur because the data is not yet being sent to the compact disc writer 90.

The second microprocessor 140 is contained on a single board computer 160 which individually includes all the components required to functionally operate a computer, as is well know in the art. The second microprocessor 140 instructs the first storage medium 150 to then transfer the data to the second computer readable storage medium 170, preferably a hard disk drive. Finally, the second microprocessor 140 directs a small computer system interface (SCSI) 180 to transfer the data from the second storage medium 170 to the compact disc writer 90 in a continuous and uninterrupted bit stream.

Referring to FIG. 3, alternative embodiments of the present invention are illustrated. In this regard, two compact disc writers 190 may be electrically connected to the tower-based PC 70 for permitting each writer 190 to sequentially write the same data to each disk. In another embodiment, a digital video camera 200 replaces the x-ray equipment for supplying digital video images to the PC 70.

The invention has been described with reference to a preferred embodiment. However, it will be appreciated that variations and modifications can be effected by a person of ordinary skill in the art without departing from the scope of the invention.

Parts List 10 x-ray sensor
20 x-rays
30 subject
40 sensor
50 transmission device
60 fiber optic cable
70 tower-based PC
80 cable
90 compact disc writer
100 compact disc
110 PC motherboard
120 PC card
121 slot
122 interface
124 interface
130 microprocessor
140 microprocessor
150 computer readable storage medium
160 single board computer
170 computer readable storage medium
180 SCSI
190 compact disc writer
200 video camera

I claim:

1. A system for writing data to a storage media comprising:
   (a) a data acquisition device for acquiring digitized data;
   (b) a media writing device for inputting the digitized data to the storage media; and
   (c) a computer comprising:
      (c1) a first microprocessor for controlling operations of said computer;
      (c2) a first storage device for receiving and storing the digitized data from said data acquisition device;
      (c3) a second storage device for receiving and storing the digitized data from the first storage device, and for transferring the digitized data to said waiting device after the first storage device transfers the digitized data to the second storage device for substantially eliminating writing errors due to buffer underrun; and
      (c4) a second microprocessor for communicating with said first microprocessor, said media writing device and said second storage device for directing the transfer of the digitized data from the second storage device to said media writing device.

2. The system as in claim 1 further comprising a second microprocessor for communicating with said first microprocessor, said media writing device and said second storage device for directing the transfer of the digitized data from the second storage device to said media writing device.

3. The system as in claim 1, wherein said data acquisition device is x-ray equipment.

4. The system as in claim 3, wherein said storage media is a compact disc-read only memory.

5. The system as in claim 1, wherein said data acquisition device is a video camera.

6. A computer for directing and controlling operations of writing data to a storage media, the computer comprising:
   (a) a first microprocessor for controlling operations of said computer;
   (b) a first storage device for receiving and storing digitized data to be input to the storage media;
   (c) a second storage device for receiving and storing the digitized data from the first storage device, and for transferring the digitized data therefrom after the first storage device transfers the digitized data to the second storage device for ultimately permitting writing of the digitized data to the storage media for substantially eliminating writing errors due to buffer underrun; and
   (d) a second microprocessor for communicating with the first microprocessor and said second storage device for directing the transfer of the digitized data out of the second storage media after the first storage device transfers the digitized data to the second storage device.

7. The computer as in claim 6 further comprising a second microprocessor for communicating with the first microprocessor and said second storage device for directing the transfer of the digitized data out of the second storage media after the first storage device transfers the digitized data to the second storage device.

8. The computer as in claim 6 further comprising a small cable system interface for permitting communication of the computer with a media writing device.